(12) United States Patent
Modrak et al.

(10) Patent No.: US 7,683,044 B2
(45) Date of Patent: *Mar. 23, 2010

(54) SPHINGOMYELIN THERAPY OF AUTOIMMUNE DISEASE

(75) Inventors: David E. Modrak, Nutley, NJ (US); David M. Goldenberg, Mendham, NJ (US)

(73) Assignee: Center for Molecular Medicine and Immunology, Belleville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/857,303

(22) Filed: Sep. 18, 2007

(65) Prior Publication Data

US 2008/0096845 A1 Apr. 24, 2008

Related U.S. Application Data

(60) Continuation-in-part of application No. 10/366,704, filed on Feb. 14, 2003, now Pat. No. 7,288,534, which is a division of application No. 09/533,799, filed on Mar. 24, 2000, now Pat. No. 6,541,462.

(60) Provisional application No. 60/126,189, filed on Mar. 25, 1999.

(51) Int. Cl.
*A01N 57/26* (2006.01)

(52) U.S. Cl. .................................................. 514/78

(58) Field of Classification Search .................. 514/78
See application file for complete search history.

(56) References Cited

U.S. PATENT DOCUMENTS

| | | | |
|---|---|---|---|
| 5,543,152 A | 8/1996 | Webb et al. | |
| 5,631,394 A | 5/1997 | Wei et al. | |
| 5,677,337 A | 10/1997 | Wei et al. | |
| 5,681,589 A | 10/1997 | Wei et al. | |
| 5,785,987 A | 7/1998 | Hope et al. | |
| 6,121,329 A | 9/2000 | Fujii et al. | |
| 6,541,462 B1 | 4/2003 | Modrak | |

FOREIGN PATENT DOCUMENTS

| | | | |
|---|---|---|---|
| WO | WO-91/04019 | * | 4/1991 |
| WO | WO 9521175 | | 8/1995 |
| WO | WO 9845463 | | 10/1998 |

OTHER PUBLICATIONS

Hostetler et al., "Therapeutic Peptides and Proteins", Apr. 4, 1991, International Application Published Under the PCT WO 91/04019.*
Conti-Fine et al.,"Myasthenia gravis: past, present, and future", Nov. 2006, Journal of Clinical Investigation, vol. 116 No. 11, pp. 2843-2854.*
Dorner et al., "Targeting CD22 as a Strategy for Treating Systemic Autoimmune Diseases", 2007, Therapeutics and Clinical Management, vol. 3 No. 5, pp. 953-959.*
Modrak, D. E., et al., "Sphingomyelin Potentiation of Chemotherapy in HT-29 Bearing Nude Mice," Proceedings of the American Association for Cancer Research, vol. 40, Mar. 1999, pp. 483-484.
Elorza, B., et al., "Characterization of 5-fluorouracil loaded liposomes prepared by referse-phase evaporation or freezing-thawing extrusion methods: study of drug release" Biochim. et Biophys. Acta, 1153 (1993), pp. 135-142.
Anghileri, L. J., "$Ca^{2+}$-Transport Inhibition by the Antitumor Agents Adriamycin and Daunomycin," Arzneim-Forsch./ Drug Res. 27 (I), Nr. 6 (1977) pp. 1177-1180.
Cheung, Benny C. L., et al., "Loading of Doxorubicin into Liposomes by Forming $Mn^{2+}$-drug Complexes" B.C.L. Cheung et al. I Biochim. Biophys. Acta 1414 (1998), pp. 205-216.
Ichinose, Yasufumi, et al., "Apoptosis Induction in Synovial Fibroblasts by Ceramide: In vitro and in vivo Effects" J Lab Clin Med, vol. 131, No. 5, May 1998, pp. 410-416.
Mizushima, Noboru, et al., "Ceramide Induces Apoptosis of Synovial Cells" Arthritis and Rheumatism, vol. 39, No. 9 Suppl., 1996, pge S80, XP009064949.
Database WPI Section Ch, Week 198320 Derwent Publications Ltd., London GB, An 1983-47914K XP002376061.
Partial European Search Report, EP 06075201.
Kinya Koizumi et al., "Rapid Isolation and Lipid Characterization of Plasma Membranes From Normal and Malignant Lymphoid Cells of Mouse," Biochim. Biophys. Acta, 1981, vol. 649, pp. 393-403.
Wim J. Van Blitterswijk et al., "Differences in Membrane Lipid Composition and Fluidity of Transplanted GRSL Lymphoma Cells, Depending on Their Site of Growth in the Mouse," Biochim. Biophys. Acta, 1984, vol. 778, pp. 521-529.

(Continued)

*Primary Examiner*—Johann R Richter
*Assistant Examiner*—Ali Soroush
(74) *Attorney, Agent, or Firm*—Richard A. Nakashima

(57) ABSTRACT

Autoimmune disease therapy in a patient treated with apoptosis-inducing agents is enhanced by co-administration of sphingomyelin. The combination most likely enhances an autoimmune disease cell's ability to undergo ceramide-induced apoptosis by increasing the levels of sphingomyelin in all cellular compartments, thereby providing sufficient substrate for activated sphingomyelinase. In alternative embodiments, sphingomyelin may be administered alone, in combination with corticosteroids, and/or in combination with a apoptosis-inducing agent.

34 Claims, No Drawings

OTHER PUBLICATIONS

Ali Bettaieb et al., "Opposite Effects of Tumor Necrosis Factor alpha on the Sphingomyelin-Ceramide Pathway in Two Myeloid Leukemia Cell Lines: Role of Transverse Sphingomyelin Distribution in the Plasma Membrane," Blood, 1996, vol. 88, pp. 1465-1472.

Modrak, D.E. et al., "Sphingomyelin potentiation of chemotherapy in HT-29 bearing nude mice," Proceedings of the American Association For Cancer Research Annual Meeting, 90th Annual Meeting of the American Association for Cancer Research, Philadelphia, PA, Apr. 1999.

Elorza, B. et al., "Characterization of 5-fluorouracil loaded liposomes prepared by reverse-phase evaporation or freezing-thawing extrusion methods: Study of drug release," Biochim. Biophys. Acta, 1993, vol. 1153, No. 2, pp. 135-142.

Anghileri, L.F., "Ca 2+ transport inhibition by the antitumor agents adriamycin and daunomycin," Arzneimittel-Forschung/Drug Research, 1977, vol. 27, No. 6, pp. 1177-1180.

Cheung, C.L. et al., "Loading of doxorubicin into liposomes by forming MN2+-drug complexes," Biochim. Biophys. Acta, 1998, vol. 1414, pp. 205-216.

* cited by examiner though the sphingomyelin is unable to be acted upon by the sphingomyelin hydrolyzing enzymes responsible for generating
SPHINGOMYELIN THERAPY OF AUTOIMMUNE DISEASE

RELATED APPLICATIONS

This application is a continuation-in-part of U.S. patent application Ser. No. 10/366,704 (now issued U.S. Pat. No. 7,288,534), filed on Feb. 14, 2003, which was a divisional of U.S. patent application Ser. No. 09/533,799 (now issued U.S. Pat. No. 6,541,462), filed Mar. 24, 2000, which claimed the benefit under 35 U.S.C. 119(e) of U.S. Provisional Application Ser. No. 60/126,189, filed on Mar. 25, 1999, the text of each of the priority application is incorporated herein by reference in its entirety.

FIELD OF THE INVENTION

The present invention relates to methods and compositions for treatment of autoimmune disease, comprising administering a therapeutic amount of sphingomyelin to a subject with an autoimmune disease. In preferred embodiments, the sphingomyelin is administered in combination with one or more therapeutic agents that induce apoptosis. The methods and compositions are applicable for therapy of autoimmune disease in general, including but not limited to immune-mediated thrombocytopenia, acute idiopathic thrombocytopenic purpura, chronic idiopathic thrombocytopenic purpura, myasthenia gravis, lupus nephritis, lupus erythematosus, rheumatoid arthritis, Goodpasture's syndrome, Graves disease, Sjogren's syndrome and multiple sclerosis.

BACKGROUND OF THE INVENTION

Traditionally, the efficacy of many cancer therapies was believed to arise from the cytotoxicity derived from chemotherapy- or radiation-induced DNA damage. Such DNA damage was considered to trigger an apoptotic response. See Eastman et al., Cancer Invest., 10: 229-240 (1992); Allan, D. J., Int. J. Radiat. Biol., 62: 145-152 (1992). Apoptosis is conceptualized as an inducible preprogrammed pathway of sequential biochemical events, leading to activation of calcium- and magnesium-dependent endonucleases that cleave the nuclear chromatin at selective internucleosomal linker sites. Signals generated at the membrane of the affected cell activate neighboring cells and infiltrating macrophages to phagocytize the dying cell and its disintegrating nucleus.

An early hypothesis on the nature of the lethal damage produced by ionizing radiation identified heterologous double strand breaks in the DNA as the most common type of lesions that lead to mammalian cell death. See Radford, I. R., Int. J. Radiat. Biol., 49: 611-620 (1986); Ward, J. F., Prog. Nucleic Acid Mol. Biol., 35: 95-125 (1988). Such lesions are produced in the DNA by direct interaction with X-rays, or with reactive oxygen intermediates generated within the cell by the radiation. See Steel et al., Int. J. Radiat. Biol., 56: 525-537 (1989). While mammalian cells are proficient in repairing most DNA double strand breaks, not all such lesions are repairable. See Ward, J. F., Prog. Nucleic Acid Mol. Biol., 35: 95-125 (1988). Residual unrepaired DNA lesions can lead to postmitotic cell death. See Bedford, J. S., Int. J. Radiat. Oncol. Biol. Phys., 21: 1457-1469 (1991). Therefore, until recently, inefficiency of DNA repair was thought to play a key role in radiation sensitivity.

Similarly, some chemotherapies, for example anthracycline daunorubicin (DNR), were believed to induce cytotoxicity as a result of drug-induced damage to DNA. It was suggested that damage to genetic material could result from free radicals stemming from the quinone-generated redox activity, from intercalation-induced distortion of the double helix, or from stabilization of the cleavable complexes formed between DNA and topoisomerase II. See Chabner et al., Cancer: Principles and Practice of Oncology, J. B. Lippencott Co., Philadelphia, Pa. Pp 349-395 (1989). However, the mechanism by which such damage induced the apoptotic pathway remained unclear.

In recent years, an alternative to the hypothesis that direct DNA damage from cancer therapies mediates induced apoptosis has been established. The sphingomyelin signal transduction pathway for induction of apoptosis has emerged as a leading mechanism in many cancer therapies, including ionizing radiation, autoimmune disease necrosis factor α (TNF-α) and daunorubicin. See Haimovitz-Friedman et al., J. Exp. Med., 180: 525-535 (1994); Kolesnick et al., Cell, 77: 325-328 (1994); Jaffrezou et al., Embo J., 15: 2417-2424 (1996); Bose et al., Cell, 82: 405-414 (1995).

Sphingomyelin is a class of sphingolipids, which constitute a major lipid class in the cell, especially the plasma membrane. See Merrill et al., Toxicol. Appl. Pharmcol., 142: 208-225 (1997). Sphingomyelin is compartmentalized into two distinct pools in the plasma membrane. See Linardic et al., J. Biol. Chem., 269: 23530-23537 (1994). It has been proposed that the sphingomyelin pool localized to the inner leaflet of the plasma membrane is dedicated exclusively to intracellular signaling. Alternatively, it has been suggested that inner leaflet, mitochondrial and/or nuclear sites of ceramide production may be involved in induction of apoptosis. (Modrak et al., Mol. Cancer. Ther. 5:200-08, 2006). The observation that there is no difference in sphingomyelin molecular species between the two pools of sphingomyelin in the plasma membrane suggests the importance of compartmentalization in signal transduction. See Fritzgerald et al., Lipids, 30: 805-809 (1995).

Many cancer therapies initiate the sphingomyelin pathway by inducing the rapid hydrolysis of sphingomyelin to ceramide. Ceramide plays a pivotal role in a variety of cellular processes, including regulating programmed cell death. See Merrill et al., Toxicol. Appl. Pharmcol., 142: 208-225 (1997). The specificity of ceramide as a second messenger for apoptosis was demonstrated by the fact that cell-permeable ceramide analogs, but not analogs of other lipid second messengers, were able to recapitulate the effects of TNF-α, Fas, and ionizing radiation and induce apoptosis directly. Induction of apoptosis by ceramide is also stereospecific, since dihydroceramide fails to induce apoptosis. It has been proposed that ceramide initiates apoptosis by activating the stress-activated protein kinase pathway. See Verheij et al., Nature, 380: 75-79 (1996). The role of sphingolipid metabolism in cancer therapy has recently been summarized (Modrak et al., Mol. Cancer. Ther. 5:200-8, 2006).

While many therapies are successful in initiating the sphingomyelin transduction pathway, the induced apoptotic response may be limited or short-lived. For unknown reasons, tumor cells have abnormal lipid composition, including sphingomyelin. Tumor tissues typically have higher concentrations of sphingomyelin than normal tissues; however, it is possible that some tumor cells have reduced sphingomyelin synthesis capabilities. See Koizumi et al., Biochim. Biophys. Acta., 649: 393-403 (1991); Van Blitterswijk et al., Biochim. Biophys. Acta., 778: 521-529 (1984). Additionally, altered lipid metabolism in tumor cells can result in changes in the intracellular distribution of sphingomyelin. Such redistribution within the plasma membrane can lead to misdirected sphingomyelin which is unable to be acted upon by the sphingomyelin hydrolyzing enzymes responsible for generating ceramide in response to cytotoxic treatment. See Bettaieb et al., Blood, 88: 1465-1472 (1996). Consequently, sphingomyelin re-organization within the plasma membrane can impair a tumor cell's ability to generate ceramide-induced apoptosis and lead to reduced sensitivity to certain therapies.

Similarities exist between autoimmune disease and certain types of cancer, such as B-cell or T-cell lymphomas or leukemias. The pathogenic roles of T- and B-cells in human autoimmune disease may involve a variety of mechanistic pathways (e.g., Martin and Chan, Immunity 20:517-27, 2004; McFarland and Martin, Nat. Immunol. 8:913-19, 2007; Stinissen et al., Crit. Rev. Immunol. 17:33-75, 1997). There is reason to believe that therapies targeted against T- and B-cells may have common effects on lymphomas and leukemias and on various autoimmune diseases in which T- or B-cells play a role in etiology. However, previous studies have not identified or characterized a cumulative or synergistic effect between apoptosis-inducing therapeutic agents that affect T- or B-cells and ceramide pathway agents, such as sphingomyelin, on either T- or B-cell related cancers or autoimmune disease. A need exists in the field for effective methods and compositions utilizing apoptosis-inducing therapeutic agents and sphingomyelin for therapy of autoimmune disease.

SUMMARY OF THE INVENTION

The claimed methods and compositions resolve a need in the art for effective therapies directed against autoimmune disease, such as by administration of sphingomyelin, alone or in combination with one or more therapeutic agents that induce apoptosis. In various embodiments, the therapeutic agent may be a cytotoxic chemotherapeutic agent, a naked antibody, antibody fragment or fusion protein, an antibody, antibody fragment or fusion protein conjugated to a therapeutic agent, ionizing radiation, radioimmunotherapy or any other known pro-apoptosis agent. In preferred embodiments, sphingomyelin also acts to induce apoptosis and exhibits a cumulative effect with other pro-apoptotic agents. In more preferred embodiments, the therapeutic agent may be 5-fluorouracil, doxorubicin, gemcitabine, methotrexate, cyclophosphamide, azacytidine, corticosteroids, TNF-$\alpha$ inhibitors, nitrogen mustards, nitrosoureas, platinum compounds, azathioprine, mercaptopurine, dactinomycin, anthracyclines, mitomycin C, bleomycin, mithramycin, cyclosporin, FK506, rapamycin, interferon-$\alpha$, interferon-$\beta$, interferon-$\gamma$, mycophenolate, FTY720 or antibodies against T- or B-cell antigens, as well as against human leukocyte antigen (HLA), including invariant chain (CD74).

In various embodiments, the subject with autoimmune disease may be a human or other mammalian subject and the autoimmune disease may include, but is not limited to, immune-mediated thrombocytopenia, acute idiopathic thrombocytopenic purpura, chronic idiopathic thrombocytopenic purpura, myasthenia gravis, lupus nephritis, lupus erythematosus, rheumatoid arthritis, Goodpasture's syndrome, Graves disease, Sjogren's syndrome and multiple sclerosis.

Certain embodiments concern a method of enhancing autoimmune disease therapy in a mammalian patient, comprising administering to the patient in conjunction with therapy with an apoptosis inducing therapeutic agent, a therapeutically effective amount of sphingomyelin. In preferred embodiments, the above method may be used for enhancing autoimmune disease therapy selected from one or more of the following: chemotherapy, ionizing radiation, immunotherapy and radioimmunotherapy. In various embodiments, the therapeutic agent may comprise or be attached to an antibody, antibody fragment or antibody fusion protein with affinity for one or more antigens associated with or expressed on a T-cell or a B-cell, or a macrophage, such as CD3 (e.g., OKT3 antibody), CD4, CD19, CD20, CD22, CD25, CD40L, CD52, CD74, HLA-DR, CTLA4 or IL-2a, as well as antibodies against macrophage migration inhibition factor (MIF). It is contemplated that such antibodies may be monospecific (bind to only one target antigen), bi-specific (bind to two antigens) or multi-specific (bind to multiple antigens). The skilled artisan will realize that although co-administration of sphingomyelin with an apoptosis inducing therapeutic agent is preferred, in other embodiments sphingomyelin alone may be administered for therapy of autoimmune diseases.

In one embodiment, naturally occurring sphingomyelin (C16:0) is administered alone or along with the autoimmune disease therapy. In another embodiment, sphingomyelin molecules with shorter side chains ($C_2$-$C_{15}$) are utilized.

In yet another embodiment, sphingomyelin is administered to a patient orally or parenterally.

In certain embodiments, there is provided a method of treating rheumatoid arthritis in a mammalian patient, comprising administering to the patient an amount of sphingomyelin effective to increase ceramide production and resultant apoptosis.

In another embodiment, there is provided a pharmaceutical composition comprising an amount of sphingomyelin effective to enhance apoptosis in a mammalian patient, for use in conjunction with pro-apoptotic autoimmune disease therapy. There is provided also a pharmaceutical composition comprising an amount of sphingomyelin effective to increase ceramide production and resultant apoptosis in mammals.

In other embodiments, there are provided kits useful for enhancing autoimmune disease therapy, comprising sphingomyelin and ancillary reagents to effect administration of the sphingomyelin.

Other objects, features and advantages of the present invention will become apparent from the following detailed description. It should be understood that examples are given by way of illustration only, since various changes and modifications within the spirit and scope of the invention will become apparent to those skilled in the art.

DETAILED DESCRIPTION

Autoimmune Disease Therapy with Sphingomyelin

The claimed methods and compositions enhance autoimmune disease therapy. The methods and compositions are believed to enhance an autoimmune cell's ability to undergo ceramide-induced apoptosis by increasing the levels of sphingomyelin in all cellular compartments, thereby providing sufficient substrate for activated sphingomyelinase. While most autoimmune cells may have endogenous levels of sphingomyelin, it may be unavailable to its hydrolyzing enzyme, sphingomyelinase, due to subcellular compartmentalization of sphingomyelin. The alteration of sphingomyelin metabolism can impair an autoimmune cell's ability to generate ceramide and can lead to reduced sensitivity to certain therapies. Surprisingly and unexpectedly, the present results demonstrate that administration of additional sphingomyelin increases the efficacy of autoimmune disease therapy.

In accordance with one embodiment, the activity of an apoptosis-inducing autoimmune disease therapy is increased by administering to the patient a therapeutically effective amount of sphingomyelin along with the therapy. While not limited to any proposed mechanism, the administration of sphingomyelin is likely to enhance any therapy which utilizes the sphingomyelin signal transduction pathway for induction of apoptosis. This includes, but is not limited to, therapies which seek to control or inhibit rapid cell growth, such as chemotherapy, ionizing radiation, immunotherapy and radioimmunotherapy, and cell-mediated therapy of viral infection.

In a preferred embodiment, a therapeutically effective amount of sphingomyelin is administered to a patient undergoing autoimmune disease treatment with chemotherapy. Sphingomyelin can be co-administered with a variety of chemotherapies. Examples include, but are not limited to, epipodophyllotoxins (e.g., etoposide, tenoposide), anthracyclines (e.g., doxorubicin/adriamycin, daunorubicin, idarubicin), Vinca alkaloids (e.g., vincristine, vinblastine), camptothecins, taxanes (e.g., Taxol) and metabolic inhibitors (e.g., 5FU, gemcitabine). In a more preferred embodiment, the effect of therapy with sphingomyelin and an apoptosis-inducing agent is synergistic, with the cumulative effect greater than the sum of the effects of either agent alone. Particularly preferred are therapeutic agents known for use with autoimmune diseases such as rheumatoid arthritis, including but not limited to methotrexate, cyclophosphamide, azacytidine, corticosteroids, TNF-$\alpha$ inhibitors (e.g., Etanercept, Infliximab, D2E7, Adalumimab), IL-1 blockers (e.g. Anakinra, Enbrel, IL1-Ra), nitrogen mustards, nitrosoureas, platinum compounds, azathioprine, mercaptopurine, dactinomycin, mitomycin C, bleomycin, mithramycin, cyclosporine, FK506, rapamycin, interferon-$\alpha$, interferon-$\beta$, interferon-$\gamma$, mycophenolate, D-penicillamine, hydroxychloroquine, leflunomide, minocycline, sulfasalazine and FTY720. In some embodiments, sphingomyelin may be administered alone or with a low dose of prednisone or prednisolone.

In a further embodiment, the chemotherapy may be targeted to autoimmune disease cells, such as T- or B-cells, or macrophages, using an antibody or antibody fragment. Use of antibodies, antibody fragments, or receptor binding peptides to specifically target autoimmune disease cells increases the delivery of chemotherapeutic agents while causing a significant reduction of toxicity to normal tissues. Particularly preferred are antibodies or fragments against antigens preferentially expressed by T- or B-cells, such as CD3 (e.g., OKT3 antibody), CD4, CD19, CD20, CD22, CD25, CD40L, CD52, CD74, HLA-DR, CTLA4 or IL-2a.

In another preferred embodiment, a therapeutically effective amount of sphingomyelin is administered to a patient undergoing autoimmune disease treatment with ionizing radiation. A variety of sources may be used to generate ionizing radiation for the purpose of autoimmune disease therapy. Examples include, but are not limited to, external beam radiation.

In still another preferred embodiment of the present invention, a therapeutically effective amount of sphingomyelin is administered to a patient undergoing autoimmune disease treatment with immunotherapy. Such treatment, utilizing unconjugated antibodies and antibody fragments, effectively induces cells to undergo apoptosis by cross-linking selected surface receptors, for example the TNF receptor. Antibodies of potential use include Muromonab (anti-CD3), Priliximab (anti-CD4), Zanolimumab (anti-CD4), Efalizumab (Raptiva, anti-CD11a), MT103 (anti-CD19), humanized anti-CD19 antibody (e.g., U.S. Pat. No. 7,109,304, incorporated herein by reference), Veltuzumab (anti-CD20), Rituximab (Rituxan, anti-CD20), Tositumomab (anti-CD20), Epratuzumab (anti-CD22), anti-CD40L antibody (e.g., U.S. Pat. No. 6,645,494, incorporated herein by reference), anti-CD45 antibody (see, e.g., U.S. Pat. No. 7,160,987, incorporated herein by reference; see also YAML568, Glatting et al., J. Nucl. Med. 47:1335-41, 2006), Alemtuzumab (Campath, anti-CD52), Milatuzumab (anti-CD74), hL243 (anti-HLA-DR, e.g., U.S. Ser. No. 11/368,296, filed Mar. 3, 2006, incorporated herein by reference), Basiliximab (Simulect, anti-IL-2 receptor), Enbrel (anti-TNF), Adalimumab (Humira, anti-TNF$\alpha$), Infliximab (Remicade, anti-TNF$\alpha$) and Natalizumab (Tysabri, anti-VLA4 receptor).

In yet another preferred embodiment, a therapeutically effective amount of sphingomyelin is administered to a patient undergoing autoimmune disease treatment with radioimmunotherapy. Radioimmunotherapy is an attractive therapeutic concept which offers advantages over more traditional forms of autoimmune disease treatment. The strategy seeks to deliver doses of radiation to autoimmune disease cells, such as T- or B-cells, with reduced radiation toxicity to normal tissues. Radioimmunotherapy utilizes antibodies, antibody fragments, or receptor binding peptides to specifically target autoimmune disease cells. The antibodies, etc., are conjugated to radioisotopes which ideally provide sufficient irradiation to kill autoimmune disease cells. Such radiolabeled antibodies, as well as receptor-binding peptides (e.g., somatostatin analogs) have been shown to selectively target disease cell populations in animal models and in humans. See Goldenberg, D. M. (editor), Cancer imaging with radiolabeled antibodies. Kluwer Academic Publishers, Boston (1990); Goldenberg, D. M. (editor), Cancer Therapy with Radiolabeled Antibodies. CRC Press: Boca Raton (1995); Krenning et al., J. Nucl. Med., 33: 652-658 (1992); Sharkey and Goldenberg Calif. Cancer J. Clin. 56:226-43 (2006). As discussed above, ionizing radiation can initiate apoptosis using the sphingomyelin transduction pathway. Therefore, administering sphingomyelin with radioimmunotherapy will increase the efficacy of such treatment.

The effectiveness of a variety of autoimmune disease therapies can be increased by coadministering to the patient a therapeutically effective amount of sphingomyelin along with the therapy. Examples of such therapies include, but are not limited to, oxygen radicals (e.g., $O_2^-$, NO), cytokines (e.g., FAS, TNF$\alpha$, TRAIL), protein phosphatase inhibitors (e.g., okadaic acid), retinoids (e.g., fenretinide), steroids (e.g., $\beta$-Sitosterol), corticosteroids (e.g., hydrocortisone, cortisone acetate, prednisone, prednisolone, meytlprednisolone, dexamethasone, betamethasone, triamcinolone, beclometasone, fludrocortisones acetate, deoxycorticosterone acetate, aldosterone), dimethylsphingosine, $\Delta$9-Tetrahydrocannabinol, suramin, sodium butyrate, platinum compounds (e.g., cis-platin, carboplatin), immunomodulators (e.g., cyclosporin, FK506), toxins (e.g., shiga-, vero-, Pseudomonas endo-) and phthalocyanine 4-photodynamic therapy. Sphingomyelin also can be used in conjunction with multidrug resistance modulators which increase ceramide levels and potentiate apoptosis (e.g., SDZ PSC 833, VX710).

In another embodiment, a therapeutically effective amount of sphingomyelin is administered to a patient suffering from rheumatoid arthritis. The disease is characterized by a proliferation of synovial cells and an infiltration of inflammatory cells that leads to cartilage and bone destruction. Abnormal events within the apoptotic process can result in the proliferation of rheumatoid synovial fibroblasts. C2-ceramide has been shown to induce apoptosis in rheumatoid synovial fibroblasts in vitro and in vivo. See Ichinose et al., J. Lab. Clin. Med., 131: 410-416 (1998). Administration of sphingomyelin is believed to increase ceramide production and, therefore, can provide an effective treatment for rheumatoid arthritis by promoting apoptosis in proliferating synovial fibroblasts. Similarly, sphingomyelin administration can effectively treat other autoimmune diseases which result from ineffective utilization of the sphingomyelin signal transduction pathway for induction of apoptosis. In this embodiment, sphingomyelin can be administered systemically or, preferably, intralesionally, such as into the arthritic joint, either alone or in combination with an anti-arthritic agent that is preferred for intralesional administration, such as radioactive gold or another cytotoxic radiopharmaceutical, a cytotoxic drug, a therapeutic antibody, a TNF-α inhibitor, or a receptor antagonist, such as IL-1α (Enbrel).

In one embodiment, naturally occurring sphingomyelin is administered to a patient to enhance the efficacy of autoimmune disease therapy. Naturally occurring sphingomyelin typically contains long, side chain derivatives ($C_{16}$-$C_{30}$ N-acyl groups). Such sphingomyelin can be obtained from commercial sources and is usually derived from egg yolk and contains primarily palmitoyl chains. See Sigma Chemicals (St. Louis, Mo.), Catalog # S0756. Other sources of sphingomyelin include Avanti Polar Lipids (Alabaster, Ala.), Lipoid GmbH (Ludwigshafen, Germany) and Matreya (Pleasant Gap, Pa.). Sphingomyelin may be purified and formulated for human use by standard procedures.

The de novo biosynthesis of sphingomyelin is initiated by the condensation of serine and palmitoyl-CoA resulting in the formation of 3-ketosphinganine (3-ketodihydrosphingosine), which is subsequently reduced to dihydrosphingosine. See Hannun, Y. A., J. Biol. Chem., 269: 3125-3218 (1994). Dihydroceramide is formed by the amide linkage of fatty acyl groups to dihydrosphingosine. Ceramide is formed from dihydroceramide by the introduction of the trans-4,5-double bond and serves as a precursor for all other complex sphingolipids. Sphingomyelin is formed by the addition of a phosphorylcholine head group to ceramide primarily through the transfer of choline phosphate from phosphatidylcholine through the action of phosphatidylcholine:ceramide choline phosphotransferase.

In another embodiment, sphingomyelin with modified side chains can be administered to a patient to enhance the efficacy of autoimmune disease therapy. For example, sphingomyelin analogs with shorter-than-normal side chains, including $C_2$-$C_{15}$ side chains, can be utilized. Apoptotic studies have shown that ceramide analogs with short side chains ($C_2$, $C_8$) effectively induce apoptosis and may act more rapidly than normal length molecules. See Bose et al., Cell, 82: 405-414 (1995); Haimovitz-Friedman et al., J. Exp. Med., 180: 525-535 (1994). Similarly, sphingomyelin analogs with shorter-than-normal side chains offer a further enhancement of the efficacy of autoimmune disease therapy agents. Alternatively, longer-than-normal side chains, including $C_{24}$, also can be effective.

Numerous strategies are well-known in the art for altering the activity of biological molecules by modifying their structure. In general, modifications to a naturally occurring compound can increase its biological activity or facilitate its uptake by appropriate cell machinery. Besides varying the length of a molecule's side chains, incorporating additional elements or functional groups also can enhance the performance of a naturally occurring compound. Examples of such substituents include, but are not limited to, aliphatic groups, e.g., $C_1$-$C_6$ straight or branched chain alkyl or cycloalkyl groups, aromatic groups, functional groups, e.g., cyano-, nitro-, azido-, halo- and epoxy-groups, and other elements, e.g., sulfur, selenium, boron and metals, as well as insertion of, e.g., oxygen or nitrogen atoms in the side chains. Sphingomyelin activity also can be enhanced by adding double or triple bonds to the molecule. See Kishida et al., J. Lipid Mediat. Cell Signal, 16: 127-137 (1997).

In one embodiment, sphingomyelin is administered to a patient orally. In another embodiment, it is administered parenterally. Parenteral administration refers to a variety of methods of administering a compound to a patient including, but not limited to, administration intravenously/intra-arterially, intrathecally, subcutaneously, intralesionally (as in a diseased joint), and via a transdermal patch.

In another embodiment, gene therapy is used to increase the sphingomyelin concentration within target cells of a patient undergoing autoimmune disease therapy. Gene therapy requires a system for introducing a vector containing an enzyme involved in the synthesis of sphingomyelin into target cells. Any enzyme, including those of mammalian, bacterial or fungal origin, which increases the concentration of sphingomyelin in a cell can be used. Examples include, but are not limited to, serinepalmitoyltransferase, ceramide synthase and sphingomyelinase.

The construction of a suitable vector can be achieved by any of the methods well-known in the art for the insertion of exogenous DNA into a vector. See Sambrook et al., 1989, Molecular Cloning, A Laboratory Manual, Cold Spring Harbor Press, NY. In addition, the prior art teaches various methods of introducing exogenous genes into cells in vivo. See Rosenberg et al., Science 242:1575-1578 (1988); Wolff et al., PNAS 86:9011-9014 (1989). The routes of delivery include systemic administration and administration in situ. Well-known techniques include systemic administration with cationic liposomes, and administration in situ with viral vectors. See Caplen et al., Nature Med., 1:39-46 (1995); Zhu et al., Science, 261:209-211 (1993); Berkner et al., Biotechniques, 6:616-629 (1988); Trapnell et al., Advanced Drug Delivery Rev., 12:185-199 (1993); Hodgson et al., BioTechnology 13: 222 (1995). Vectors and gene delivery systems which specifically direct the exogenous genes to target cells are most preferred. It is anticipated that future developments in targeted gene delivery will increase the significance of this embodiment.

A "therapeutically effective" amount of sphingomyelin can be determined by prevention or amelioration of adverse conditions or symptoms of diseases, injuries or disorders being treated. Optimization of the timing and dosage of sphingomyelin administered to a patient in conjunction with autoimmune disease therapy by convention is adapted to, among other things, the particular characteristics of the patient and the extent of the autoimmune disease. Such adaptations are routine and do not require undue experimentation or skill in the art. The methods and pharmaceutical compositions can be used to treat a variety of mammals and are used most preferably to treat humans and domesticated animals, such as livestock and pets.

Liposomes can be combined with inert pharmaceutical excipients such as lactose, oil, mannitol and starch to form pharmaceutical compositions/preparations. Such compositions can be formulated into dosage forms such as elixirs, liquids, ointments, lotions, IV fluids, alcohol, tablets, capsules, and the like. For parenteral, intramuscular, subcutaneous and intravenous administration, the liposomes can be formulated with an inert, parenterally acceptable vehicle such as water, saline, sesame oil, ethanol buffered aqueous medium, propylene glycol and the like. For topical and oral administration, the liposomes can be formulated with waxes, oils, buffered aqueous medium, and the like. These various pharmaceutical dosage forms are prepared by methods well-known to the pharmacist's art.

In another embodiment, there is provided a kit useful for enhancing autoimmune disease therapy, comprising sphingomyelin and ancillary reagents to effect administration of the sphingomyelin. Examples of ancillary reagents include, but are not limited to, buffered solutions and application devices, such as syringes. Such ancillary reagents may also comprise one or more apoptosis-inducing therapeutic agents.

Antibody-Based Therapy Targeted Against T- or B-Cells, or Macrophages

Various embodiments may concern the use of antibodies, antibody fragments or antibody fusion proteins that bind to various expressed antigens of cells associated with autoimmune disease, for example T- or B-cells. B-cell clones that bear autoantibody Ig-receptors are present in normal individuals. Autoimmunity results when these B-cells become overactive, and mature to plasma cells that secrete autoantibody. Similarly, activated T-cells are known to be involved in the development of various autoimmune diseases, such as multiple sclerosis, rheumatoid arthritis and systemic lupus erythematosus (e.g., Steinman, 1993, Sci. Amer. 9:107-114). An exacerbation in autoimmune patients is believed to start when autoreactive T cells are activated (e.g., U.S. Pat. No. 6,645,494). It has been proposed that autoantigen-specific T cells may be selectively destroyed by using antibodies against the CD40L antigen (U.S. Pat. No. 6,645,494).

In accordance with certain embodiments, autoimmune disorders can be treated by administering an antibody that binds to a T- or B-cell antigen, or a macrophage antigen, such as the CD3, CD4, CD19, CD20, CD22, CD25, CD40L, CD52, CD74, HLA-DR, CTLA4, MIF, or IL-2a antigen. In one embodiment, comparatively low doses of an entire, naked antibody or combination of entire, naked antibodies are used. In other embodiments, conjugates of such antibodies with drugs, toxins or therapeutic radioisotopes are useful. Bispecific antibody fusion proteins which bind to the T- or B-cell antigens, or to macrophage antigens, can be used, including hybrid antibodies which bind to more than one T- or B-cell, or macrophage, antigen. Preferably the bispecific and hybrid antibodies additionally target a T-cell, plasma cell or macrophage antigen. The methods also are directed to multimodal therapeutic methods in which the antibody administration is supplemented by administration of other therapeutic modalities.

As used herein, "antibody" encompasses naked antibodies and conjugated antibodies and antibody fragments, which may be monospecific or multispecific. It includes both polyclonal and monoclonal antibodies, as well as certain recombinant antibodies, such as chimeric and humanized antibodies and fusion proteins.

A chimeric antibody is a recombinant protein that contains the variable domains and complementary determining regions derived from a rodent antibody, while the remainder of the antibody molecule is derived from a human antibody.

Humanized antibodies are recombinant proteins in which murine complementarity determining regions of a monoclonal antibody have been transferred from heavy and light variable chains of the murine immunoglobulin into a human variable domain.

A naked antibody is an antibody which is not conjugated with a therapeutic agent. Naked antibodies include both polyclonal and monoclonal antibodies, as well as certain recombinant antibodies, such as chimeric and humanized antibodies. Similarly, a naked antibody fragment or naked fusion protein is an antibody fragment or fusion protein that is not conjugated to a therapeutic agent. In certain embodiments, such naked antibodies, antibody fragments or fusion proteins may be administered in combination with other antibodies, fragments or fusion proteins or with a different type of apoptosis-inducing therapeutic agent.

A fusion protein is a recombinantly produced antigen-binding molecule in which two or more different single-chain antibody or antibody fragment segments with the same or different specificities are linked. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

Production of Anti-T- or B-cell Antibodies

T- or B-cell antibodies of use include numerous antibodies known in the art, such as Enbrel (anti-TNF), Adalimumab (anti-TNFα), Alemtuzumab (anti-CD52), Basiliximab (anti-IL-2 receptor), Efalizumab (anti-CD 11a), Infliximab (anti-TNFα), Muromonab (anti-CD3), Natalizumab (anti-VLA4 receptor) and Rituximab (anti-CD20). Anti-CD20, anti-CD22, anti-CD19, anti-CD3, anti-CD4, anti-CD25, CD40L, anti-HLA-DR, anti-CTLA4, anti-IL-2a and anti-CD74 antibodies are known generally to those of skill in the art. See, for example, Ghetie et al., Cancer Res. 48:2610 (1988); Hekman et al., Cancer Immunol. Immunother. 32:364 (1991); Kaminski et al., N. Engl. J. Med. 329:459 (1993); Press et al., N. Engl. J. Med. 329:1219 (1993); Maloney et al., Blood 84:2457 (1994); Press et al., Lancet 346:336 (1995); Longo, Curr. Opin. Oncol. 8:353 (1996), and any such known antibodies may be utilized in the claimed methods and compositions. More particularly, rodent monoclonal antibodies to CD3, CD4, CD19, CD20, CD22, CD25, CD40L, CD52, CD74, HLA-DR, CTLA4 or IL-2a antigens can be obtained by methods known to those skilled in the art. See generally, for example, Kohler and Milstein, Nature 256:495 (1975), and Coligan et al. (eds.), CURRENT PROTOCOLS IN IMMUNOLOGY, VOL. 1, pages 2.5.1-2.6.7 (John Wiley & Sons 1991) ["Coligan"]. Briefly, monoclonal antibodies can be obtained by injecting mice with a composition comprising the antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen that was injected, culturing the clones that produce antibodies to the antigen, and isolating the antibodies from the hybridoma cultures. MIF has been described as having a role in inflammation, cancer, and autoimmune diseases (Bucala and Donnelly, Immunity 26:281-5, 2007), and which can be inhibited with anti-MIF antibodies (see, e.g., U.S. Pat. Nos. 6,492,428; 6,599,938; 6,645,493 and 6,774,227).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

Suitable amounts of well-characterized antigen for production of antibodies can be obtained using standard techniques. As an example, CD22 can be immunoprecipitated from B-lymphocyte protein using the deposited antibodies described by Tedder et al., U.S. Pat. No. 5,484,892 (1996).

Alternatively, CD3, CD4, CD19, CD20, CD22, CD25, CD40L, CD52, CD74, HLA-DR, CTLA4 MIF, or IL-2a antigen proteins can be obtained from transfected cultured cells that overproduce the antigen of interest. Expression vectors that comprise DNA molecules encoding each of these proteins can be constructed using published nucleotide sequences. See, for example, Wilson et al., J. Exp. Med. 173:137 (1991); Wilson et al., J. Immunol. 150:5013 (1993). As an illustration, DNA molecules encoding CD22 can be obtained by synthesizing DNA molecules using mutually priming long oligonucleotides. See, for example, Ausubel et al., (eds.), CURRENT PROTOCOLS IN MOLECULAR BIOLOGY, pages 8.2.8 to 8.2.13 (1990) ["Ausubel"]. Also, see Wosnick et al., Gene 60:115 (1987); and Ausubel et al. (eds.), SHORT PROTOCOLS IN MOLECULAR BIOLOGY, 3rd Edition, pages 8-8 to 8-9 (John Wiley & Sons, Inc. 1995). Established techniques using the polymerase chain reaction provide the ability to synthesize genes as large as 1.8 kilobases in length. Adang et al., Plant Molec. Biol. 21:1131 (1993); Bambot et al., PCR Methods and Applications 2:266 (1993); Dillon et al., "Use of the Polymerase Chain Reaction for the Rapid Construction of Synthetic Genes," in METHODS IN MOLECULAR BIOLOGY, Vol. 15: PCR PROTOCOLS: CURRENT METHODS AND APPLICATIONS, White (ed.), pages 263-268, (Humana Press, Inc. 1993).

In a variation of this approach, monoclonal antibody can be obtained by fusing myeloma cells with spleen cells from mice immunize with a murine pre-B cell line stably transfected with cDNA which encodes the antigen of interest. See Tedder et al., U.S. Pat. No. 5,484,892 (1996).

One example of a suitable murine anti-CD22 monoclonal antibody is the LL2 (formerly EPB-2) monoclonal antibody, which was produced against human Raji cells derived from a Burkitt lymphoma. Pawlak-Byczkowska et al., Cancer Res. 49:4568 (1989). This monoclonal antibody has an $IgG_2\alpha$ isotype, and the antibody is rapidly internalized into lymphoma cells. Shih et al., Int. J. Cancer 56:538 (1994). Immunostaining and in vivo radioimmunodetection studies have demonstrated the excellent sensitivity of LL2 in detecting B-cell lymphomas. Pawlak-Byczkowska et al., Cancer Res. 49:4568 (1989); Murthy et al., Eur. J. Nucl. Med. 19:394 (1992). Moreover, $^{99m}$Tc-labeled LL2-Fab' fragments have been shown to be useful in following upstaging of B-cell lymphomas, while $^{131}$I-labeled intact LL2 and labeled LL2 F(ab')$_2$ fragments have been used to target lymphoma sites and to induce therapeutic responses. Murthy et al., Eur. J. Nucl. Med. 19:394, (1992); Mills et al., Proc. Am. Assoc. Cancer Res. 34:479 (1993) [Abstract 2857]; Baum et al., Cancer 73 (Suppl. 3):896 (1994); Goldenberg et al., J. Clin. Oncol. 9:548 (1991). Furthermore, Fab' LL2 fragments conjugated with a derivative of Pseudomonas exotoxin has been shown to induce complete remissions for measurable human lymphoma xenografts growing in nude mice. Kreitman et al., Cancer Res. 53:819 (1993). The use of humanized LL2 (epratuzumab) for therapy of cancer and immune dysfunction disease has been recently reviewed. (D. M. Goldenberg, Expert Rev. Anticancer Ther. 5:1341-53, 2006). Epratuzumab has exhibited efficacy against non-Hodgkin's lymphoma, systemic lupus erythematosus and primary Sjogren's syndrome. An example of an anti-CD74 antibody is the LL1 antibody. A humanized version of LL1 (hLL1) is known as milatuzumab (see, e.g., U.S. Pat. No. 6,653,104, incorporated herein by reference).

In an additional embodiment, an antibody is a chimeric antibody in which the variable regions of a human antibody have been replaced by the variable regions of a rodent anti-CD22 antibody. The advantages of chimeric antibodies include decreased immunogenicity and increased in vivo stability.

Techniques for constructing chimeric antibodies are well known to those of skill in the art. As an example, Leung et al., Hybridoma 13:469 (1994), describe how they produced an LL2 chimera by combining DNA sequences encoding the VK and VH domains of LL2 monoclonal antibody with respective human kappa and IgG constant region domains. This publication also provides the nucleotide sequences of the LL2 light and heavy chain variable regions.

In yet another embodiment, an antibody is a "humanized" monoclonal antibody. That is, mouse complementarity determining regions are transferred from heavy and light variable chains of the mouse immunoglobulin into a human variable domain, followed by the replacement of some human residues in the framework regions of their murine counterparts. Humanized monoclonal antibodies in accordance with this invention are suitable for use in therapeutic methods. General techniques for cloning murine immunoglobulin variable domains are described, for example, by the publication of Orlandi et al., Proc. Nat'l Acad. Sci. USA 86: 3833 (1989). Techniques for producing humanized monoclonal antibodies are described, for example, by Jones et al., Nature 321:522 (1986), Riechmann et al., Nature 332:323 (1988), Verhoeyen et al., Science 239:1534 (1988), Carter et al., Proc. Nat'l Acad. Sci. USA 89:4285 (1992), Sandhu, Crit. Rev. Biotech. 12:437 (1992), Singer et al., J. Immun. 150:2844 (1993), and Qu et al., Methods 36:84-95 (2005). The publication of Leung et al., Mol. Immunol. 32:1413 (1995), describes the construction of humanized LL2 antibody (epratuzumab).

In another embodiment, an antibody is a human monoclonal antibody. Such antibodies are obtained from transgenic mice that have been "engineered". to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994).

Production of Bispecific Antibodies

Various embodiments also may employ a bispecific antibody (bsAb) or antibody fragment (bsFab) having at least one arm that specifically binds to a T- or B-cell antigen and at least one other arm that specifically binds a targetable conjugate. The targetable conjugate comprises a carrier portion which comprises or bears at least one epitope recognized by at least one arm of the bispecific antibody or antibody fragment. In a preferred embodiment, the epitope is a hapten. In an alternative embodiment, the epitope is a part of the carrier. Examples of recognizable haptens include, but are not limited to, chelators, such as DTPA, fluorescein isothiocyanate, vitamin B-12 and other moieties to which specific antibodies can be raised. The carrier portion also may be conjugated to a variety of agents. Examples of conjugated agents include, but are not limited to, metal chelate complexes, drugs, toxins and other effector molecules, such as cytokines, lymphokines, chemokines, immunomodulators, radiosensitizers, asparaginase, carboranes and radioactive halogens. Additionally, enzymes useful for activating a prodrug or increasing the target-specific toxicity of a drug can be conjugated to the carrier. Thus, the use of bispecific antibodies and fragments which have at least one arm that specifically binds a targetable conjugate allows a variety of therapeutic and diagnostic applications to be performed without raising new bsAb for each application.

A more recent method of making and using bispecific or multispecific constructs is known as the dock-and-lock technology (U.S. patent application Ser. Nos. 11/389,358, filed Mar. 24, 2006; 11/391,584, filed Mar. 28, 2006; 11/478,021, filed Jun. 29, 2006; 11/633,729, filed Dec. 5, 2006, the text of each of which is incorporated herein by reference.

Certain embodiments encompasses antibodies and antibody fragments. The antibody fragments are antigen binding portions of an antibody, such as F(ab')2, F(ab)2, Fab', Fab, and the like. The antibody fragments bind to the same antigen that is recognized by the intact antibody. For example, an anti-CD22 monoclonal antibody fragment binds to an epitope of CD22. The bsAb of the present invention include, but are not limited to, IgG×IgG, IgG×F(ab')2, IgG×Fab', IgG×scFv, F(ab')$_2$×F(ab')$_2$, Fab'×F(ab')$_2$, Fab'×Fab', Fab'×scFv and scFv×scFv bsMabs. Also, species such as scFv×IgG×scFv and Fab'×IgG×Fab', scFv×F(ab')$_2$×scFv and Fab'×F(ab')$_2$×Fab' are included.

The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("sFv proteins"), and minimal recognition units consisting of the amino acid residues that mimic the hypervariable region.

Production of Fusion Proteins

Another method for producing bsAbs is to engineer recombinant fusion proteins linking two or more different single-chain antibody or antibody fragment segments with the needed dual specificities. See, e.g., Coloma et al., Nature Biotech. 15:159-163, 1997. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

Functional bispecific single-chain antibodies (bscAb), also called diabodies, can be produced in mammalian cells using recombinant methods. See, e.g., Mack et al., Proc. Natl. Acad. Sci., 92: 7021-7025, 1995. For example, bscAb are produced by joining two single-chain Fv fragments via a glycine-serine linker using recombinant methods. The V light-chain (VL) and V heavy-chain (VH) domains of two antibodies of interest are isolated using standard PCR methods. The VL and VH cDNA's obtained from each hybridoma are then joined to form a single-chain fragment in a two-step fusion PCR. The first PCR step introduces the (Gly4-Ser1)3 linker, and the second step joins the VL and VH amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into chinese hamster ovary cells. Recombinant methods can be used to produce a variety of fusion proteins.

Coupling of Antibodies to Lipid Emulsions

Long-circulating sub-micron lipid emulsions, stabilized with poly(ethylene glycol)-modified phosphatidylethanolamine (PEG-PE), can be used as drug carriers for antibodies. The emulsions are composed of two major parts: an oil core, e.g., triglyceride, stabilized by emulsifiers, e.g., phospholipids. The poor emulsifying properties of phospholipids can be enhanced by adding a biocompatible co-emulsifier such as polysorbate 80. In a preferred embodiment, the antibody is conjugated to the surface of the lipid emulsion globules with a poly(ethylene glycol)-based, heterobifunctional coupling agent, poly(ethylene glycol)-vinylsulfone-N-hydroxy-succinimidyl ester (NHS-PEG-VS). In more preferred embodiments, the liposomes may be used as delivery vehicles to deliver a selected amount of sphingomyelin to the target cell or tissue.

The submicron lipid emulsion is prepared and characterized as described. Lundberg, J. Pharm. Sci., 83:72 (1993); Lundberg et al., Int. J. Pharm., 134:119 (1996). The basic composition of the lipid emulsion is triolein:DPPC:polysorbate 80, 2:1:0.4 (w/w). When indicated, PEG-DPPE is added into the lipid mixture at an amount of 2-8 mol % calculated on DPPC. Methods to conjugate liposomes loaded with a cytotoxic drug with a suitable cell-targeting antibody, such as against CD74 (Fab' fragment of LL1) have been described in Lundberg et al., Drug Deliv 14:171-5 (2007).

The coupling procedure starts with the reaction of the NHS ester group of NHS-PEG-VS with the amino group of distearoyl phosphatidyl-ethanolamine (DSPE). Twenty-five μmol of NHS-PEG-VS are reacted with 23 μmol of DSPE and 50 μmol triethylamine in 1 ml of chloroform for 6 hours at 40° C. to produce a poly(ethylene glycol) derivative of phosphatidyl-ethanolamide with a vinylsulfone group at the distal terminus of the poly(ethylene glycol) chain (DSPE-PEG-VS). For antibody conjugation, DSPE-PEG-VS is included in the lipid emulsion at 2 mol % of DPPC. The components are dispersed into vials from stock solutions at −20° C., the solvent is evaporated to dryness under reduced pressure. Phosphate-buffered saline (PBS) is added, the mixture is heated to 50° C., vortexed for 30 seconds and sonicated with a MSE probe sonicator for 1 minute. Emulsions can be stored at 4° C., and preferably are used for conjugation within 24 hours.

Coupling of antibodies to emulsion globules is performed via a reaction between the vinylsulfone group at the distal PEG terminus on the surface of the globules and free thiol groups on the antibody. Vinylsulfone is an attractive derivative for selective coupling to thiol groups. At approximately neutral pH, VS will couple with a half life of 15-20 minutes to proteins containing thiol groups. The reactivity of VS is slightly less than that of maleimide, but the VS group is more stable in water and a stable linkage is produced from reaction with thiol groups.

Before conjugation, the antibody is reduced by 50 mM 2-mercaptoethanol for 10 minutes at 4° C. in 0.2 M Tris buffer (pH 8.7). The reduced antibody is separated from excess 2-mercaptoethanol with a Sephadex G-25 spin column, equilibrated in 50 mM sodium acetate buffered 0.9% saline (pH 5.3). The product is assayed for protein concentration by measuring its absorbance at 280 mm (and assuming that a 1 mg/ml antibody solution of 1.4) or by quantitation of $^{125}$I-labeled antibody. Thiol groups are determined with Aldrithiol™ following the change in absorbance at 343 mm and with cystein as standard.

The coupling reaction is performed in HEPES-buffered saline (pH 7.4) overnight at ambient temperature under argon. Excess vinylsulfone groups are quenched with 2 mM 2-mercaptoethanol for 30 minutes, excess 2-mercaptoethanol and antibody are removed by gel chromatography on a Sepharose CL-48 column. The immunoconjugates are collected near the void volume of the column, sterilized by passage through a 0.45 μm sterile filter, and stored at 4° C.

Coupling efficiency is calculated using $^{125}$I-labeled antibody. Recovery of emulsions is estimated from measurements of [$^{14}$C]DPPC in parallel experiments. The conjugation of reduced LL2 to the VS group of surface-grafted DSPE-PEG-VS is very reproducible with a typical efficiency of near 85%.

The therapeutic compositions described herein are useful for treatment of autoimmune diseases, particularly for the treatment of Class III autoimmune diseases including immune-mediated thrombocytopenias, such as acute idiopathic thrombocytopenic purpura and chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigus, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis (Graves disease), scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis. In this context, the therapeutic compositions are used to deplete the blood of normal T- or B-cells for an extended period.

Although naked, anti-CD4, anti-CD20, anti-CD22, ant-CD25 anti-CD74, anti-CTLA4 or anti-HLA-DR antibodies are a preferred therapeutic composition for treatment of autoimmune diseases, the efficacy of such naked antibody therapy can be enhanced by supplementing the naked antibodies with other therapies described herein, such as administration of sphingomyelin. In such multimodal regimens, the supplemental therapeutic compositions can be administered before, concurrently or after administration of the naked antibodies. Multimodal therapy of Class III autoimmune diseases may comprise co-administration of therapeutics that are targeted against T-cells, plasma cells or macrophages, such as antibodies directed against T-cell epitopes, more particularly against the CD4, CD5, CD25 or CTLA4 epitopes. Where B-cells are targeted, antibodies against CD20, CD22, CD74 or HLA-DR are preferred. Gamma globulins also may be co-administered. In some cases, it may be desirable to co-administer immunosuppressive drugs such as corticosteroids and possibly also cytotoxic drugs. In this case, lower doses of the corticosteroids and cytotoxic drugs can be used as compared to the doses used in conventional therapies, thereby reducing the negative side effects of these therapeutics. The supplemental therapeutic compositions can be administered before, concurrently or after administration of the naked T- or B-cell antibodies, or macrophage antibodies, including MIF antibodies. In alternative embodiments, antibodies against MIF (macrophage migration inhibition factor) may be used in combination with sphingomyelin (see, e.g., U.S. Pat. Nos. 6,492,428; 6,599,938; 6,645,493 and 6,774,227).

In an alternative embodiment, the antibodies to the CD3, CD4, CD19, CD20, CD22, CD25, CD40L, CD52, CD74, HLA-DR, CTLA4, MIF, or IL-2a antigen are conjugated to a drug, toxin, enzyme, hormone, cytokine, immunomodulator, boron compound or therapeutic radioisotope, or a fusion protein of an antibody and a toxin may be used. These conjugates and fusion proteins may be used alone, or in combination with naked T- or B-cell antibodies. In a further preferred embodiment, an antibody is used that comprises an arm that is specific for a low-molecular weight hapten to which a therapeutic agent is conjugated or fused. In this case, the antibody pretargets the T- or B-cells, or macrophages, and the low-molecular weight hapten with the attached therapeutic agent is administered after the antibody has bound to the T- or B-cell, or macrophage, targets. Examples of recognizable haptens include, but are not limited to, chelators, such as DTPA, fluorescein isothiocyanate, vitamin B-12 and other moieties to which specific antibodies can be raised.

Drugs which are known to act on B-cells, plasma cells and/or T-cells are particularly useful, whether conjugated to a T- or B-cell antibody, or administered as a separate component in combination with a naked or conjugated T- or B-cell antibody. These include methotrexate, phenyl butyrate, bryostatin, cyclophosphamide, etoposide, bleomycin, doxorubicin, carmustine, vincristine, procarbazine, dexamethasone, leucovorin, prednisone, maytansinoids such as DM1, calicheamicin, rapamycin, leflunomide, FK506, immuran, fludarabine, azathioprine, mycophenolate, and cyclosporin. Drugs such as immuran, methotrexate, and fludarabine which act on both B-cells and T-cells are particularly preferred. Illustrative of toxins which are suitably employed in accordance with the present invention are ricin, abrin, ribonuclease, DNase I, Staphylococcal enterotoxin-A, pokeweed antiviral protein, gelonin, diphtherin toxin, Pseudomonas exotoxin, Pseudomonas endotoxin and RNAses, such as onconase. See, for example, Pastan et al., Cell 47:641 (1986), and Goldenberg, CA—A Cancer Journal for Clinicians 44:43 (1994), Sharkey and Goldenberg Calif. Cancer J. Clin. 56:226-43 (2006). Other suitable drugs and toxins are known to those of skill in the art.

Cytokine agonists and antagonists may also be used in multimodal therapies according to the present invention. Tumor necrosis factor alpha (TNF-α) and interleukin-1 (IL-1) are important in mediating inflammation in rheumatoid arthritis. Accordingly, anti-TNF-α reagents, such as Infliximab (Remicade), Adalimumab (Humira) and Etanercept (Enbrel) are useful in multimodal therapy, as well as anti-IL-1 reagents (e.g., anakinra).

Other useful secondary therapeutics useful in multimodal therapies are IL-2 and GM-CSF, which may be conjugated with an anti-T- or B-cell, or macrophage antibody, or combined with a naked anti-T- or B-cell, or macrophage, antibody as a separate component.

In general, the dosage of administered antibodies will vary depending upon such factors as the patient's age, weight, height, sex, general medical condition and previous medical history. Typically, it is desirable to provide the recipient with a dosage of antibody component, immunoconjugate or fusion protein which is in the range of from about 1 pg/kg to 15 mg/kg (amount of agent/body weight of patient), although a lower or higher dosage also may be administered as circumstances dictate, such as in the range of 2 mg/kg to 10 mg/kg.

Administration of antibodies to a patient can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses. Intravenous injection provides a useful mode of administration due to the thoroughness of the circulation in rapidly distributing antibodies. Oral formulations and administrations of sphingomyelin are also of use, but generally require an increased dose, such as 5 mg/kg to 20 mg/kg.

In preferred embodiments, naked anti-B-ell antibodies, particularly anti-CD22 or anti-CD20 antibodies, are administered at protein doses, such as 100 milligrams to 1 gram protein per dose, given once, or repeatedly, parenterally. Alternatively, naked antibodies are administered in doses of 20 to 1500 milligrams protein per dose, or 20 to 500 milligrams protein per dose, or 20 to 100 milligrams protein per dose.

EXAMPLES

Example 1

Therapy of Rheumatoid Arthritis with Sphingomyelin

Preparation of Sphingomyelin

Various forms of sphingomyelin can be obtained in powder form from Sigma Chemicals (St. Louis, Mo.). Mix 1 g of sphingomyelin powder with 9.5 ml of sterile saline or phosphate buffered saline (PBS) and QS to 10 ml. Sonicate the resulting suspension in a water bath at 80-90° C. for 1 hour. The suspension should be administered within one hour of sonication and should be approximately room temperature (25-30° C.). The suspension can be stored at 4° C.; however, it should be re-sonicated for 30 minutes in a water bath at 80-90° C. before administration.

Alternatively, liposomes of the present invention can be prepared using an extruding machine. Such machines are available from a variety of sources, e.g., AmiKa Corporation, Columbia, Md. These machines produce small, unilaminar vesicles/liposomes of defined size.

Treatment of Rheumatoid Arthritis

Patient W R is a 58-year-old woman with a prior history of no major illnesses other than recurrent allergies and having 3 prior pregnancies that were uneventful and resulted in 3 healthy children. She has a history of rheumatoid arthritis (RA) that presented about 5 years ago, and has undergone numerous treatments with corticosteroids, cyclophosphamide, and methotrexate, with responses of reduced durations and then relapses. She now presents to her rheumatologist with active RA as judged by the presence of 5 tender and 4 swollen joints (out of 44 examined), morning stiffness for more than 45 minutes, an elevated erythrocyte sedimentation rate (ESR) of 40 mm/h (Westergren method), and an elevated C-reactive protein (CRP) blood level of 80 mg/L, as well as increased levels of rheumatoid factor (RF) of IgM, IgG, and IgA isotypes. All other laboratory tests, except circulating red blood cells (mild anemia), are within the normal range. She has been taking a nonsteroidal anti-inflammatory drug (NSAID; ibuprofen), 20 mg/day of prednisolone, and doses of cyclophosphamide i.v. (750 mg).

The patient is allowed to continue on these medications, and is also given i.v. infusions of sphingomyelin (prepared as described above) in phosphate-buffered sterile saline and QS twice weekly at doses of 400 mg, continuing for 3 weeks. At 4 and 6 weeks later, the patient returns for evaluation, and shows improvements in the ACR20 score by 20%, including about a 50% improvement in the elevated CRP, RF, and ESR levels, and reduction of joint stiffness in the morning to less than 15 minutes. The therapy of prednisolone, NSAID, and sphingomyelin is repeated at 3 months, and the patient then shows even further improvement when evaluated at 4 and 6 months following the onset of management, such that her ESR, CRP, and RF factor levels are only about 20% above the normal range, her joint stiffness and swelling is reduced by about 50% as compared to baseline, and in general she is functioning with less joint pain and restrictions. The patient is considered to have improved upon adding sphingomyelin i.v. therapy to her prior medications, to which she relapsed. Subsequently, she has her prednisolone maintenance therapy tapered to 5 mg daily with 200 mg sphingomyelin given 3 times weekly for 8 weeks, and is able to function as before without any deterioration of her condition, with increase in her physical activities and general reduction in joint pain and swelling. The addition of sphingomyelin to the patient's standard anti-rheumatoid therapeutic agents unexpectedly shows a more than additive effect, compared with either sphingomyelin or standard anti-rheumatoid therapeutic agents alone. This surprising result suggests that sphingomyelin treatment acts to potentiate the effect of apoptosis-inducing agents for treatment of rheumatoid arthritis and other autoimmune diseases.

Example 2

Therapy of Systemic Lupus Erythematosus (SLE) with Sphingomyelin

R. S. is a 47-year-old African American female with two healthy children, and with a history of SLE for at least 8 years. She has received prior cyclophosphamide, azathioprine, and corticosteroid treatments, with recurrent activity flares resulting in increasing disability. She has had evidence of myelosuppression, with lymphopenia, resulting in tapering of her medications. Prior to receiving the current experimental therapy, she is confirmed to have a diagnosis of SLE according to the American College of Rheumatology revised criteria, and moderately active disease (a score of 10 for total British Isles Lupus Assessment Group (BILAG) disease activity) at study entry. Her current medication of prednisolone, 15 mg/day, is continued, and she receives epratuzumab (anti-CD22 humanized monoclonal antibody) i.v. at 360 mg/m$^2$ once weekly every other week for a total of 4 infusions. Prior to each infusion, she is medicated with acetaminophen (Tylenol) and antihistamine (Benadryl). She is also given an infusion of 300 mg sphingomyelin twice weekly for 8 weeks. Two and 6 weeks after completion of this therapy, she is evaluated, and it is decided that her prednisolone doses of 15 mg/day can be tapered to 10 mg/day, because of initial evidence of improvement of her BILAG scores in 3 of the 8 body systems. Four weeks later, the SLE panel of tests (autoantibodies, C3, C-reactive protein, erythrocyte sedimentation rate), and physical examination indicate progressive improvement, with less fatigue, lethargy, malaise, anorexia, reduction of malar erythemia, and reduction of arthritis. She is considered to have about a 40% improvement of her condition as a result of the investigational therapy. Surprisingly, the combination of sphingomyelin with prednisolone and epratuzumab is more effective than either agent alone and indicates a synergistic effect of sphingomyelin with apoptosis-inducing agents for treatment of SLE.

Example 3

Therapy of Rheumatoid Arthritis with Adalimumab Combined with Sphingomyelin

A 54-year-old Caucasian woman with 3 healthy children presents with a history of rheumatoid arthritis (RA) for 9 years, and a prior therapy history of methotrexate, leflunomide, prednisolone, sometimes in combination. She continues on her methotrexate (10 mg) and prednisolone (10 mg) daily doses, and is now given the TNF antagonist, adalimumab (Humira, Abbott Laboratories) subcutaneously at 40 mg every other week, combined with weekly infusions of sphingomyelin at a dose of 400 mg. This therapy is continued for 12 weeks, and she is evaluated for response every 4 weeks after completion of her course of therapy by ACR 20%, 50% and 70% scoring, and EULAR responses. The therapy is tolerated well, and the patient has tapering of her prednisolone to 5 mg daily at 6 weeks of therapy, and an ACR50 improvement and a moderate EURAR response by the end of the 12-week course. She continues on her maintenance therapy of methotrexate and prednisolone for another 8 weeks, and shows continued improvement at her 6-month evaluation, and is deemed as a good response to the anti-TNF therapy combined with sphingomyelin.

Example 4

Therapy of Primary Sjogren's Syndrome (pSS)

A 58-year-old female with a 9-year history of pSS with prior courses of therapy with immunosuppressive drugs (cyclophosphamide, methotrexate, corticosteroids) presents with active disease and is given a course of 10 mg methotrexate and 15 mg prednisolone daily for 4 weeks, and does not appear to respond objectively, but only says her dry mouth and dry eyes appear to be improved slightly. She then receives a course of rituximab (Rituxan, Genentech) at 600 mg infused over 6 hours every other week for 3 doses, combined with weekly infusions of sphingomyelin at doses of 400 mg for 6 weeks. During this therapy, only 15 mg prednisolone is continued as a maintenance therapy. After the first rituximab infusion, her circulating B-cells are measured to be depleted by 90%, which continues for about 8 months. Her main subjective symptoms of dry mouth and eyes show improvement, as well as her parotid gland reduction is noted, and also an improvement in her dry cough and purpura. An improvement of the objective parameters of dry eyes and dry mouth is also observed, and this improvement is maintained for at least 3 months after this therapy course. The combination of sphingomyelin with apoptosis-inducing agent is shown to be synergistic for treatment of pSS.

Example 5

In-Vitro Evaluation of Sphingomyelin Therapy on B-Cells

Sphingomyelin enhancement of chemotherapy is evaluated by measuring its effect on 5-fluorouracil or doxorubicin (DOX) treatment of B-cells isolated from individuals with autoimmune disease and grown in culture. Cell viability is measured using the dye MTT (3-(4,5-dimethylthiazol-2-yl)-2,5-diphenyl tetrazolium bromide) in a 24-well chamber format. See Mosmann, T., J. Immunol. Methods, 65:55-63 (1983). B-cells are maintained in RPMI media supplemented with 10% fetal calf serum. Human umbilical cord venous endothelial cells (HUVEC) from pooled donors (Clonetics/BioWhittaker, San Diego, Calif.) are used as controls. Cells ($10^4$/well) are plated in the presence of varying concentrations of drug and sphingomyelin and grown in a humidified incubator. As an additional control, egg yolk phosphatidylcholine (PC) (Sigma, St. Louis, Mo.) is added to the cells instead of sphingomyelin. Drugs and lipids are added to HUVEC cells 24 hours after plating, but otherwise are treated the same. After four days, the media is replaced with media containing 0.5 mg/ml MTT and incubated two to four hours at 37° C. An equal volume of 0.04 N HCl in isopropanol is added, and the absorbance at 570 nm is measured. The $IC_{50}$ values, defined as the concentration of drug necessary to reduce cell viability by 50%, from three to seven independent experiments are averaged and compared using ANOVA.

Sphingomyelin sensitizes B-cells to both 5FU and DOX. Sphingomyelin increases 5FU and DOX sensitivity in B-cells (140% and 340%, respectively). Sphingomyelin does not sensitize HUVEC cells to 5FU or DOX therapy. The enhancement of chemosensitivity appears to be a function of the ceramide portion of sphingomyelin, since PC does not elicit a similar effect as sphingomyelin.

Example 6

Treatment of a Patient with Chronic Idiopathic Thrombocytopenia Purpura

A 50-year-old female with chronic idiopathic thrombocytopenia purpura has been treated with gamma globulins and high-dose dexamethasone, but the disease progresses. She undergoes splenectomy, which fails to stabilize the disease. Her platelet count falls to less than 20,000/microliter, and hemorrhagic events increase in frequency. The patient is then treated with epratuzumab, 480 mg intravenously each week, plus 400 mg/wk of sphingomyelin, for a period of six weeks. Four weeks after the last dose of epratuzumab and sphingomyelin, platelet number is increased by 300%, and the hemorrhagic events disappear. Three months after the last treatment the disease is in full remission.

Example 7

Treatment of a Patient with Progressive Rheumatoid Arthritis

A 60-year-old male, with severe progressive rheumatoid arthritis of the finger joints, wrists, and elbows, has failed therapy with methotrexate, and obtains only minor relief when placed on Enbrel therapy. The patient is then treated with veltuzumab (anti-CD20 humanized Mab, 80 mg intravenously each week, plus 400 mg/wk of sphingomyelin, for a period of eight weeks. After 3 weeks a 30% improvement in measures of disease activity is observed, which is maintained for 6 months. The patient is again treated with veltuzumab and sphingomyelin, at the same dose and frequency. The patient continues to improve, and 6 months after the second therapy, a 70% improvement is observed. No human anti-veltuzumab antibodies are observed at any time during, or after the veltuzumab therapy. Although normal B-cells are significantly reduced from the blood, no infectious complications, or other drug-related toxicity are observed.

Example 8

Treatment of a Patient with Myasthenia Gravis

A 55-year-old male has failed all conventional therapy for myasthenia gravis, and is admitted to a neurological intensive therapy unit. The patient is stabilized by plasma exchange, and is given intravenous immunoglobulin to reduce the titer of anti-acetylcholine receptor antibody. The patient remains bedridden, and is then treated with epratuzumab, 600 mg intravenously each week, plus 400 mg/wk of sphingomyelin, for a period of six weeks. One week after the last treatment, a 50% drop in B-lymphocytes is observed, and a significant drop in the titer of the anti-acetylcholine is observed. Two months after the last treatment the patient is mobile, and is released from the hospital.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

What is claimed is:

1. A method of treating an autoimmune disease, selected from the group consisting of acute idiopathic thrombocytopenic purpura, chronic idiopathic thrombocytopenic purpura, myasthenia gravis, lupus erythematosus, Sjogren's syndrome and rheumatoid arthritis, comprising administering to a subject suffering from the disease a therapeutically effective amount of sphingomyelin.

2. The method of claim 1, wherein the subject is a human subject.

3. The method of claim 1, wherein the sphingomyelin is administered orally or parenterally.

4. The method of claim 1, further comprising administering corticosteroids to the subject.

5. The method of claim 1, further comprising administering to the subject a therapeutic agent that induces apoptosis.

6. The method of claim 5, wherein the therapeutic agent is 5-fluorouracil, doxorubicin, gemcitabine, cyclophosphamide, methotrexate, a corticosteroid, a cytokine antagonist, an antibody or antibody fragment or a combination thereof.

7. The method of claim 6, wherein the naked antibody or fragment, or cytokine antagonist, is epratuzumab, adalimumab, rituximab, enbrel, alemtuzumab, basiliximab, efalizumab, infliximab, muromomab, natalizumab, veltuzumab or milatuzumab.

8. The method of claim 5, wherein the sphingomyelin is administered at the same time as the therapeutic agent that induces apoptosis.

9. The method of claim 8, wherein administration of sphingomyelin is continued after the administration of the therapeutic agent.

10. The method of claim 5, wherein the sphingomyelin enhances the apoptotic effect of the therapeutic agent.

11. The method of claim 5, wherein the therapeutic agent is an autoimmune disease therapeutic agent.

12. The method of claim 5, wherein the therapeutic agent is attached to an antibody or antibody fragment.

13. The method of claim 5, wherein the therapeutic agent is a naked antibody or antibody fragment.

14. The method of claim 13, wherein the antibody or antibody fragment binds to an antigen expressed on a B cell, a T cell, or a macrophage (including MIF).

15. The method of claim 5, wherein said sphingomyelin is administered prior to administration of said therapeutic agent.

16. The method of claim 5, wherein said sphingomyelin is effective to increase ceramide production and apoptosis in T- or B-cells, or macrophages.

17. The method of claim 5, wherein the therapeutic agent is ionizing radiation.

18. The method of claim 5, wherein the therapeutic agent is a radionuclide.

19. The method of claim 5, wherein the therapeutic agent is tumor necrosis factor α or an anti-IL-1 antagonist.

20. The method of claim 13, wherein the antibody or antibody fragment bind to CD3, CD4, CD19, CD20, CD22, CD25, CD40L, CD52, CD74, HLA-DR, CTLA4, MIF, or IL-2a.

21. The method of claim 20, wherein the CD22-binding antibody or antibody fragment is epratuzumab or an immunoreactive fragment thereof.

22. The method of claim 20, wherein the CD20-binding antibody or antibody fragment is rituximab or veltuzumab.

23. The method of claim 20, wherein the antibody or fragment is milatuzumab, humanized L243, or an anti-MIF antibody or fragment.

24. A kit for therapy of autoimmune disease comprising a therapeutically effective amount of sphingomyelin and a therapeutic agent that induces apoptosis.

25. The kit of claim 24, wherein the therapeutic agent is a cytotoxic anti-autoimmune disease agent.

26. A method of treating an autoimmune disease comprising administering to a subject suffering from the disease, selected from the group consisting of acute idiopathic thrombocytopenic purpura, chronic idiopathic thrombocytopenic purpura, myasthenia gravis, lupus erythematosus and rheumatoid arthritis, therapeutically effective amounts of sphingomyelin and an antibody, antibody fragment or fusion protein that binds to a T- or B-cell antigen, or macrophage antigen, selected from CD3, CD4, CD19, CD20, CD22, CD40L, CD52, CD74, HLA-DR, CTLA4, MIF, or IL-2a.

27. The method of claim 26, wherein the CD22-binding antibody or fragment is epratuzumab.

28. The method of claim 26, wherein the CD20-binding antibody or fragment is rituximab or veltuzumab.

29. The method of claim 26, wherein the CD74-binding antibody or fragment is milatuzumab.

30. The method of claim 26, wherein the HLA-DR-binding antibody or fragment is humanized L243.

31. The method of claim 1, wherein a therapeutically effective amount of sphingomyelin is between 200 and 400 mg.

32. The method of claim 31, wherein the therapeutically effective amount of sphingomyelin is administered weekly or twice weekly.

33. The method of claim 26, wherein a therapeutically effective amount of sphingomyelin is between 200 and 400 mg.

34. The method of claim 33, wherein the therapeutically effective amount of sphingomyelin is administered weekly or twice weekly.

* * * * *